United States Patent [19]

Polito et al.

[11] 4,081,246
[45] Mar. 28, 1978

[54] SOLID PHASE COLUMN IMMUNOASSAY PROCEDURE EMPLOYING NOVEL IMMUNOCHEMICAL COMPOSITES

[75] Inventors: Alan J. Polito, Costa Mesa; William S. Knight, Laguna Beach, both of Calif.

[73] Assignee: Beckman Instruments, Inc., Fullerton, Calif.

[21] Appl. No.: 682,830

[22] Filed: May 3, 1976

[51] Int. Cl.$^2$ .................. G01N 31/06; G01N 33/16
[52] U.S. Cl. .................. 23/230.6; 23/230 B; 23/259; 195/63; 195/DIG. 11; 424/1; 424/1.5; 424/12; 260/112 B
[58] Field of Search ............ 23/230 B, 230.6, 259; 424/1, 1.5, 12; 195/63, DIG. 11; 260/112 B

[56] References Cited

U.S. PATENT DOCUMENTS

| | | | |
|---|---|---|---|
| 3,555,143 | 1/1971 | Axen | 424/1 |
| 3,645,852 | 2/1972 | Axen | 424/1 X |
| 3,867,366 | 2/1975 | Rubenstein | 424/1 X |
| 3,896,217 | 7/1975 | Johnson | 424/1 |
| 3,904,478 | 9/1975 | Dean | 195/DIG. 11 |
| 3,914,183 | 10/1975 | Johansson | 195/DIG. 11 |
| 3,947,352 | 3/1976 | Cuatrecasas | 195/DIG. 11 |
| 3,975,511 | 8/1976 | Vann | 424/1.5 |
| 3,980,765 | 9/1976 | Broussalian | 424/1 |
| 4,002,532 | 1/1977 | Weltman | 195/63 X |

OTHER PUBLICATIONS

Catt et al., *Biochem. J.*, 100:31C (1966).
Wide et al., *Biochem. Biophys. Acta*, 130:257 (1966);
Axen et al., *Nature* (Lond.), 214:1302 (1967).
Wide, *Acta Endocrinol.* (Copenhagen) Suppl. No. 142:207 (1966).
Siegel et al., *J. Clin. Endocrinol. Metal.*. 37:526 (1972).
Weetall, *Chem. Abst.*, 77:18064y (1972).
Moore et al., *Steroids*, 20:199 (1972).
Hersh et al., *Clinica Chemica Acta*, 63:69 (1975).
Bolton et al., *Biochemical et Biophysica Acta*, 329:318 (1973).
Seligson et al., *Clinica Chemica Acta*, 38:199 (1972).
Alexander et al., *Clin. Chem.*, 20:553 (1974).
Alexander et al., *Clin. Chem.* 20:1353 (1974).
Boguslaski et al., *Analytical Chemistry*, 47(9):1583 (1975).
Boguslaski et al., *Clinica Chemica Acta*, 62:349 (1975).
Davis et al., *Clinica Chemica Acta*, 66:379 (1976).
Immobilized Enzymes, Antigens, Antibodies, and Peptides, edited by Howard H. Weetall, Marcell Decker, Inc., New York, N.Y. (1975), Chapter 4.
Immobilized Enzymes, Antigens, Antibodies, and Peptides, edited by Howard H. Weetall, Marcell Decker, Inc., New York, N.Y. (1975), Chapter 9.

*Primary Examiner*—Sidney Marantz
*Attorney, Agent, or Firm*—Robert J. Steinmeyer; Robert S. Frieman

[57] ABSTRACT

An improved method of separating free from bound fractions in a solid phase column immunoassay procedure of the type wherein a solution is contacted with a composite comprising an activated polysaccharide matrix covalently coupled to a primary antibody, wherein the improvements comprise:

(a) coupling an $\alpha,\omega$-diaminospacer to said activated polysaccharide matrix via one of said $\alpha,\omega$-diaminospacer's amino groups thereby forming a derivatized polysaccharide matrix; and (b) covalently coupling said derivatized polysaccharide matrix to an antibody selected from a group consisting of primary and secondary antibodies via a bifunctional coupling agent having a formula

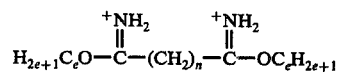

wherein $n$ is an integer from 1 and 6 and wherein $e$ is an integer from 1 to 2.

17 Claims, No Drawings

SOLID PHASE COLUMN IMMUNOASSAY PROCEDURE EMPLOYING NOVEL IMMUNOCHEMICAL COMPOSITES

BACKGROUND OF THE INVENTION

1. Field of the Invention

This invention pertains to a method of separating free from bound fractions in a solid phase column immunoassay procedure and to a novel immunochemical composite for use therein.

2. Description of the Prior Art

Solid phase radioimmunoassay (RIA) has become popular because the system in which both the antigen-antibody reaction and the separation of free and bound antigen can be achieved in a single step results not only in a simple and rapid RIA, but also eliminates a number of handling and other errors which are inherent in other separation techniques. K. J. Catt, H. D. Niall, and G. W. Tregear, *Biochem. J.*, 100:31c (1966), originally used as solid phase materials powdered polymers bearing reactive thiocyanate groups (—N=C=S) capable of forming covalent linkages with antibodies. Antibodies coupled to cyanogen-bromide-activated dextran and cellulose particles came into vogue as a result of the work of Wide, Porath, and Axen [L. Wide and J. Porath, *Biochem. Biophys. Acta*, 130:257 (1966), R. Axen, J. Porath and S. Ernback, *Nature* (Lond.), 214:1302 (1967), and L. Wide, *Acta Endocrinol.* (Copenhagen) Suppl., No. 142:207 (1969)]. Today antibodies have been covalently attached to a variety of solid matrices such as agarose, glass, polyacrylamide, and even iron oxide powder. S. J. Siegel, W. F. Line, N. S. T. Yang, A. Kwong, and C. Frank, *J. Clin. Endocrinol. Metab.*, 37:526 (1973), H. H. Weetall, *Chem. Abst.*, 77:18064y (1972), P. H. Moore and L. R. Axelrod, *Steroids*, 20:199 (1972), and L. S. Hersh and S. Yaverbaum, *Clinica Chemica Acta*, 63:69 (1975).

Although in principle first antibody linked to a solid phase represents a simple and versatile separation procedure, there are a number of disadvantages with this approach. The two questions one must answer in regard to solid phase systems using primary antibodies are, first, the possible loss of antibody activity (titer) with consequent waste of valuable antisera and, secondly, the possible reduction of sensitivity which may result with solid systems as compared with those which can be achieved using the same antisera in an aqueous solution. Recently, A. E. Bolton and W. H. Hunter, *Biochemica et Biophysica Acta*, 329:318 (1973), reported that recovery of antibody activity tended to be higher in solid preparations of antisera to hapten and small peptides than to similar solid preparations of antisera to large molecular weight protein hormones. Likewise, antisera to haptens covalently coupled to solid matrices show little or no loss in assay sensitivity when compared to the uncoupled antibody system whereas there was a dramatic loss of sensitivity when antibodies to large protein hormones were tested. These authors concluded that any loss of assay sensitivity resulting from the use of chemically attached antisera is probably caused by steric hindrance of the larger antigens.

Therefore, one of the major disadvantages against the use of solid preparations of primary antibody in RIA systems is that this method is not universal. (The approach cannot be implemented equally well for large and small molecules.) Other disadvantages which apply to all primary solid phase RIA procedures are: one must pipette an accurate amount of antibody from an insoluble suspension of gel, the assay mixture must be mechanically agitated to assure proper mixing, and centrifugation is usually required to separate the bound and free fractions.

The use of Sephadex columns in plastic syringes to bind a mixture of labeled $I^{125}$-thyroxine ($T_4$) and $T_4$ released from serum proteins by alkali, followed by a subsequent protein binding analysis with a fixed, limiting amount of thyroid binding globulin (TBG) on each column has recently been introduced. H. Seligson and D. Seligson, *Clin. Chim. Acta*, 38:199 (1972) and N. M. Alexander and J. F. Jennings, *Clin. Chem.*, 20:553 (1974). In this procedure, the Sephadex column also serves to separate free $T_4$ from the $T_4$-TBG complex. Similar tests have been developed for radiolabeled triiodothyronine ($T_3$) in which an antibody to $T_3$ is used as the competitive protein binder. N. M. Alexander and J. F. Jennings, *Clin. Chem.*, 20:1353 (1974). In both assays the Sephadex column serves to bind the mixture of antigen and label while other serum constituents are not retained by the gel. Next, a fixed amount of competitive protein binder is incubated in the void volume of the column during which the antisera and label redistribute between the column and the binder. Elution with buffer removes the antigen binder complex while the free antigen remains attached to the Sephadex column. Although this approach is readily automated, this system requires the accurate loading of equal amounts of gel in all columns. Thus, one must continuously stir the Sephadex on a magnetic stirrer while transferring the suspension with a graduated pipette.

R. C. Boguslaski and C. L. Schwartz, *Analytical Chemistry*, Vol. 47, No. 9, 1583 (1975), have recently reported on a column radioimmunoassay for the determination of digitoxin (mw 765) which employs a column of immobilized primary antibody which acts both as a reaction chamber and separation device. Similar primary antibody column RIA's have been reported for vitamin $B_{12}$ (mw 1,355), R. C. Boguslaski and C. P. Rathjen, *Clinica Chemica Acta*, 62:349 (1975), and insulin (mw ~ 6,000), J. W. Davis, J. M. Yoder, and E. C. Adams, *Clinica Chemica Acta*, 66:379 (1976). In view of the work of Bolton and Hunter, supra, this method is not universal in that assay sensitivity for large molecules (e.g., TSH having a molecular weight of 30,000) would be limited due to the properties of solid phase antibodies against large molecules.

It has been discovered that a universal solid phase column system for the separation of free and bound fractions can be obtained when one uses novel immunochemical composites containing a derivatized polysaccharide matrix and also containing positively charged imidoesters which covalently couple said derivatized polysaccharide matrix to antibodies.

SUMMARY OF THE INVENTION

This invention encompasses a method of separating free from bound fractions in a solid phase column immunoassay procedure of the type wherein a solution is contacted with a composite comprising an activated polysaccharide matrix covalently coupled to a primary antibody, wherein the improvements comprise:

(a) coupling an $\alpha,\omega$-diaminospacer to said activated polysaccharide matrix via one of said $\alpha,\omega$-diaminospacer's amino groups thereby forming a derivatized polysaccharide matrix; and (b) covalently coupling said derivatized polysaccharide matrix to an antibody selected from a group consisting of primary and secondary antibodies via a bifunctional coupling agent having a formula

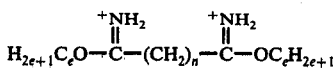

wherein $n$ is an integer from 1 and 6 and wherein $e$ is an integer from 1 to 2.

Also encompassed in this invention is an immunochemical apparatus for separating free from bound fractions in a solid phase column immunoassay procedure of the type comprising a reaction vessel and a plurality of immunochemical composites, wherein each immunochemical composite comprises an activated polysaccharide matrix covalently coupled to a primary antibody, wherein the improvements comprise:

(a) coupling an $\alpha,\omega$-diaminospacer to said activated polysaccharide matrix via one of said $\alpha,\omega$-diaminospacer's amino groups thereby forming a derivatized polysaccharide matrix; and (b) covalently coupling said derivatized polysaccharide matrix to an antibody selected from a group consisting of primary and secondary antibodies via a bifunctional coupling agent having a formula

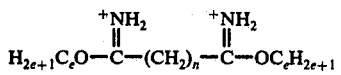

wherein $n$ is an integer from 1 and 6 and wherein $e$ is an integer from 1 to 2.

DESCRIPTION OF THE PREFERRED EMBODIMENTS

The novel immunochemical composite within the scope of this invention comprises a derivatized polysaccharide matrix covalently coupled to an antibody by a bifunctional coupling agent. The polysaccharide matrix can be any matrix having a plurality of hydroxyl groups attached thereto, as well as derivatives thereof. Preferred polysaccharide matrices include cellulosic polymers, dextran polymers, agarose, and derivatives thereof. Cellulosic polymers and derivatives thereof are the polysaccharide matrices of choice.

The polysaccharide matrices can be activated by any suitable method known to those skilled in the art. Exemplary reagents suitable for activating the polysaccharide matrix include cyanogen halide, epihalohydrin, haloacetyl halides, and divinylsulphone. See F. A. Patty, *Industrial Hygiene and Toxicology*, Vol. 2, p. 634, Interscience, New York, N. Y. (1949), R. Axen, J. Porath, and S. Ernback, *Nature* (Lond.) 214:1302 (1967), W. Rosner and R. N. Smith, *Biochem.*, 14:4813 (1975), A. Jagendorph, A. Patchornik, and M. Sela, *Biochimica et Biophysica Acta*, 78:516 (1963), and J. Porath and L. Sundberg, *Nature New Biol.*, 238:261 (1972), said publications being incorporated herein in toto by reference. Preferably, a cyanogen halide or an epihalohydrin reagent is used to activate the polysaccharide matrix. More preferably, the polysaccharide matrix is activated by an epihalohydrin reagent or mixture thereof and most preferably, the polysaccharide matrix is activated by epichlorohydrin.

The first essential requirement of this invention is the use of a derivatized polysaccharide matrix which is formed by coupling an $\alpha,\omega$-diaminospacer to the above activated polysaccharide matrix via one of the $\alpha,\omega$-diaminospacer's amino groups. To illustrate an exemplary derivatized polysaccharide matrix, if the polysaccharide matrix has been activated by a cyanogen halide reagent, the derivatized polysaccharide matrix will have the formula

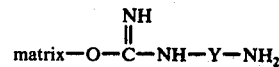

wherein matrix is a polysaccharide matrix as defined above and wherein Y is a spacer. Exemplary spacers include $-(CH_2)_M-$, $-(CH_2)_b-NH-(CH_2)_c-$,

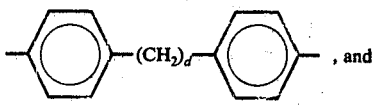, and

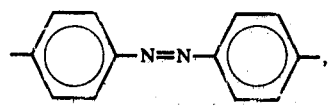, wherein $m$ is an integer from 1 to 12, preferably from 4 to 6, wherein $b$ and $c$ independently are integers from 1 to 6, preferably 2 to 3, and wherein $d$ is an integer from 1 to 10, preferably 2 to 4. Preferably, Y is $-(CH_2)_m-$.

As a further illustration of an exemplary derivatized polysaccharide matrix, if the polysaccharide matrix has been activated by an ephihalohydrin reagent, the derivatized polysaccharide matrix will have the formula

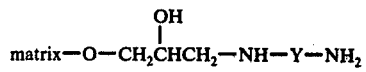

wherein matrix and Y are as defined above.

The antibody to which the derivatized polysaccharide matrix is covalently coupled can be either a primary antibody or a secondary antibody. Since this invention's sole requirement is that the antibody possess a lysine residue, virtually all primary and secondary antibodies can be covalently coupled to the derivatized polysaccharide matrix because all antibodies possess such lysine residues. Preferably, the antibody is a secondary antibody.

The second essential requirement and crux of this invention is the use of imidoesters as the coupling agent for the novel immunochemical composite. The imidoester has the general formula

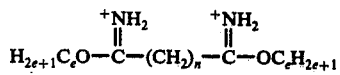

wherein $n$ is an integer from 1 to 6, preferably from 4 to 6, and wherein $e$ is an integer from 1 to 2. The use of these imidoesters enables one to covalently attach antibodies to solid supports through known chemical reactions which immobilize both primary and secondary antibodies through their lysine residues which in most instances are not essential for immunological activity. Further, the presence of a positively charged matrix does not cause adverse nonspecific adsorption onto this invention's novel immunochemical composite.

The novel immunochemical composites within the scope of this invention can be prepared in accordance with the following general procedure. An activating reagent is contacted with a polysaccharide matrix in a solution having a desirable pH. The pH can be in a general range from about 7.5 to about 10.0 with the particular pH being dictated by the activating reagent and polysaccharide matrix being used. The reaction can be allowed to proceed at room temperature. The activating reagent is allowed to remain in contact with the polysaccharide matrix for a sufficient period of time, from about 5 minutes to 5 hours, to enable the matrix to become activated. The excess activating reagene is removed from the activated polysaccharide matrix by washing said matrix with a suitable medium, e.g., water, buffer (e.g., sodium bicarbonate), etc. The activated matrix is then suspended in a suitable medium, e.g., an aqueous solution of dimethylformamide. The desired $\alpha,\omega$-diaminospacer is then added to the suspended activated polysaccharide matrix and the reaction is allowed to proceed for about 1 to 10 hours at room temperature. The excess $\alpha,\omega$-diaminospacer is removed from the derivatized polysaccharide matrix by washing said matrix with a suitable medium, e.g., a solution of dimethylformamide, followed by a washing with a suitable buffer, e.g., a sodium bicarbonate buffer. After this double washing procedure, the derivatized polysaccharide matrix is suspended in a suitable buffer, e.g., a sodium bicarbonate buffer.

The bifunctional coupling agent or mixture thereof is dissolved in a basic solution at about 4° C. If necessary, the pH is adjusted to about 8 to 9. The suspended derivatized polysaccharide matrix is then contacted with the dissolved bifunctional coupling agent and the mixture is rotated at about 4° C. for 1 to 5 hours.

After removing the excess bifunctional coupling agent, the coupled derivatized polysaccharide matrix is suspended in a mixture containing a suitable buffer, e.g., a sodium bicarbonate buffer, and a primary or secondary antibody function. The mixture is rotated for about 10 to about 24 hours in a cold environment. The immunochemical composite is then thoroughly washed with a suitable buffer, e.g., a sodium bicarbonate buffer, and then suspended in a suitable buffer having a pH of about 8, e.g., a barbital buffer containing about 0.1% gelatin.

The novel immunochemical composite within the scope of this invention and as prepared by the above general procedure has the schematic structure

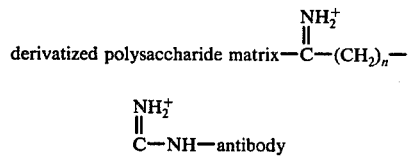

wherein derivatized polysaccharide matrix, $n$, and antibody are as defined above. The preferred immunochemical composite within the scope of this invention has a formula

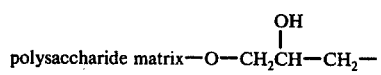

-continued
$$\text{NH—(CH}_2)_m\text{—NH—}\overset{\overset{+NH_2}{\|}}{C}\text{—(CH}_2)_n\text{—}\overset{\overset{+NH_2}{\|}}{C}\text{—NH—antibody}$$

wherein polysaccharide matrix, $m$, $n$, and antibody are as defined above.

The solid phase column immunoassay procedure of this invention entails contacting a solution containing free and bound fractions with a novel immunochemical composite via techniques well known to those skilled in the art of immunoassay and thereby separating the free from the bound fractions. See D. M. Weir, "Immunology for Undergraduates", Churchill Livingstone, Edinburgh, England (1973), J. G. Ratcliffe, *British Medical Bulletin*, 30:32 (1974), R. C. Boguslaski and C. P. Rathjen, *Clinica Chemica Acta*, 62:349 (1975) R. C. Boguslaski and L. C. Schwartz, *Analytical Chemistry*, Vol. 47, No. 9, 1583 (1975), and J. W. Davis, J. M. Yoder, and E. C. Adams, *Clinica Chemica Acta*, 66:379 (1976), said publications being incorporated herein in toto by reference. Preferably, the solid phase column immunoassay procedure is an RIA procedure which techniques are also well known to those skilled in the art. See C. S. Skelley, L. P. Brown, and P. K. Besch, "Radioimmunoassay", *Clinical Chemistry*, Vol. 19, No. 2, 146 to 186 (1973), said publication being incorporated herein in toto by reference.

As noted above, the novel immunochemical composites within the scope of this invention preferably contain second antibodies. Although there is a loss in antibody activity (titer) when a second antibody is covalently coupled to a derivatized polysaccharide matrix, consumption of second antibody is nevertheless reduced because large quantities of carrier globulin are not required as is the case for the double antibody procedure in the liquid state. Another advantage of an immunoassay procedure employing the novel solid phase second antibody columns within the scope of this invention is that this method alleviates the problem of accurately dispensing a precise amount of second antibody from a suspension of gel because in the improved method of this invention one need only have a minimal amount of second antibody. Levels above this preset minimal amount have no effect on the sensitivity or accuracy of the results obtained from this invention's novel method.

In general, novel immunochemical composites within the scope of this invention can be employed in an immunoassay procedure in accordance with the following procedure. The novel immunochemical composites within the scope of this invention are placed into any column or other suitable reaction vessel, preferably pre-washed with a suitable buffer, thereby forming this invention's novel immunochemical apparatus for separating free from bound fractions via a solid phase column immunoassay procedure. To minimize costs as well as to improve the flow rate through said column, it is preferred to also add to said column nonactivated polysaccharide matrices of various sizes. All loaded columns will have an inherent hold up volume (i.e., the maximum amount of fluid which can be retained by the column without eluting any of said fluid).

If one desires to use the novel chemical composites of this invention which contain secondary antibodies, one could preferably perform the primary immunoassay reaction outside of the column. When the primary immunoassay is performed outside of the column it can be performed in any suitable volume, preferably a final volume of 400λ. The primary immunoassay reaction can take 0.5 to 5 hours, preferably 0.5 to 1 hour, the exact time being dictated by the assay being performed. An aliquot of said reaction mixture approximately equal to said packed column's hold up volume is then added to the column and incubated on the solid phase secondary antibody column for a period of 0.5 to 1 hour, the exact time again being dictated by the assay being performed. After the incubation period, the column is washed with an appropriate amount of suitable buffer, said amount being sufficient to separate the free from bound fractions (that is being at least equal to the column's hold up volume). The column, which now contains only the bound fraction, is then capped and counted.

The reaction time for incubation of the columns can be cut very short by using an excess of bound second antibody and one can even elute immediately through the solid phase second antibody columns if an excess of second antibody is used.

The hereinbefore described immunoassay procedure employing this invention's solid phase second antibody columns can therefore be separated into three basic steps: incubation of primary antibody reaction at a station removed from the column, application of an aliquot of the reaction mixture to the solid phase second antibody column, and elution of the free fraction with buffer immediately or after a minimal incubation period on the column.

The above described solid phase second antibody procedure is simple, easily automated, precise, and versatile. Thus, both assays for large molecules (e.g., TSH) and small haptens (digoxin, $T_4$, $T_3$) can be performed using this invention's novel immunochemical composites. Furthermore, one obtains completely separate bound and free fractions with a wide margin for error in the conditions used for the separation. The method does not interfere with the primary binding reaction, is relatively inexpensive, and makes use of equipment and reagents that are readily available.

With respect to small molecules, the solid phase second antibody columns within the scope of this invention may be employed in more than one mode. The columns may be loaded with primary antibody, labeled antigen (or hapten), and sample and both the primary reaction and solid phase antibody reaction allowed to proceed simultaneously in the void volume of the column. After a given period of time, the columns are eluted with buffer to separate free from bound fractions.

Another approach is to incubate the primary antibody on the solid phase second antibody column and thus produce primary antibody columns on which the primary antibody is biologically bound to the covalently attached second antibody. Label and sample are then incubated on the columns which serve as a device for separating free and bound fractions.

In addition to the above-described method it is also within the scope of this invention to employ the novel immunochemical composites wherein said composites contain primary antibodies covalently coupled to a derivatized polysaccharide matrix.

Further, another method within the scope of this invention entails a solid phase column immunoassay procedure wherein the composite used therein is not the novel immunochemical composite described above but an immunoassay reagent comprising a polysaccharide matrix covalently coupled to a secondary antibody via any of the various techniques known to those skilled in the art. Although this latter method does not have the degree of efficacy found in the other methods of this invention, nevertheless, it is a marked improvement and possesses distinct advantages over the prior art solid phase primary column procedures.

The following examples are provided for the purpose of further illustration only and are not intended to be limitations on the disclosed invention.

EXAMPLE 1

Epichlorohydrin (3 ml) was added to a mixture of 6 gms of microcrystalline cellulose Type 50 (50μ average particle size) in 30 ml of 1N sodium hydroxide with vigorous stirring at room temperature. After 2 hours, the excess epichlorohydrin was removed by washing with 1 liter of water. The washed activated cellulosic matrix was then suspended in 60 ml of a 50% aqueous solution of dimethylformamide. To this suspended activated matrix was added 0.85 gms of 1,6-hexanediamine. The reaction was allowed to proceed with stirring for 2 hours at room temperature and then the excess 1,6-hexanediamine was removed by washing with 1 liter of a 50% aqueous solution of dimethylformamide. After washing with 1 liter of 0.1M sodium bicarbonate, the derivatized cellulosic matrix was suspended in 0.1M sodium bicarbonate to give a 1:1 mixture of derivatized matrix to sodium bicarbonate.

Dimethylsuberimidate (DMS; 0.80 gm; 3 m moles) was dissolved in 0.6 ml of cold 5N sodium hydroxide solution with stirring at 4° C. After the addition of cold 0.1 M sodium bicarbonate the pH was adjusted to 8.5 with 1N sodium hydroxide. To this solution was added 6 ml of 0.1M sodium bicarbonate containing 0.8 to 1.0 grams of derivatized cellulose and the mixture was rotated at 4° C. for 2 hours.

After the removal of excess DMS, the coupled derivatized cellulosic matrix was suspended in 9 ml of 0.1M sodium bicarbonate (4° C.) and 1.3 ml of goat antirabbit gamma globulin fraction (36 to 38 mg/ml) in 0.1M sodium bicarbonate (4° C.) and the mixture was rotated in a cold room. The immobilized second antibody was then thoroughly washed with 0.1M sodium carbonate and finally suspended in barbital buffer, pH 8.0, containing 0.1% gelatin, to give a final volume of 25 ml.

EXAMPLE 2

Procedure for the Preparation of Columns

Prewash each empty column with 1 ml of a barbital buffer containing 0.1% gelatin and 2% BSA. Wash in separate tubes both fibrous cellulose and microcrystalline cellulose Type 50. Spin down the cellulosic fractions and make 1:1 mixtures (by volume) of fibrous cellulose/buffer and microcrystalline cellulose/buffer with said buffer being a barbital buffer containing 0.1% gelatin. Then add equal volumes of the fibrous cellulose and microcrystalline cellulose mixtures to give a final mixture which can be used as a support for all columns. Each column contains the equivalent of 1.4 ml of the above mixture plus 200λ of the proper dilution of solid phase precipitating antibody. This gives a hold up volume of 300 μl. Next, each loaded column is prewashed with 1 ml of said barbital buffer containing 0.1% gelatin and 2% BSA. The columns are then capped for storage.

EXAMPLE 3

The primary RIA is done in a 400λ final volume at a space remote from the column. The primary reaction can be performed for 0.5 to 5 hours, preferably 0.5 to 1 hour. An aliquot of the primary reaction mixture (300λ) is then applied to the solid phase second antibody column. This mixture is allowed to incubate for a period of 0.5 to 1 hour. The solid phase column is then washed with 1 ml to 3 ml of said barbital buffer containing 0.1% gelatin and 2% BSA to separate the free from bound fractions. The column which now contains only the bound fractions is then capped and counted.

Data obtained by performing various tests in accordance with the general procedures outlined in the above examples is shown in Table I.

TABLE I

| | 37° Primary Assay Time Remote from Column, hr. | Room Temperature Incubation Time on Column, hr. | Control Sera | | | | |
|---|---|---|---|---|---|---|---|
| | | | Lederle I | Lederle II | Thyroxine Beckman Control Serum | TSH Beckman Control Serum | TSH Beckman Control Serum Diluted ½ |
| Digoxin (ng/ml) | ½ | ½ | 1.23 (0.8–1.3)* | 3.48 (3–3.8) | — | — | — |
| Thyroxine (μg/dl) | ½ | ½ | 8.33 (6.4–9.6) | 17.37 (13.6–22) | 20.05 (12–20) | 7.58 (6–7) | — |
| Triiodo thyronine (ng/dl) | 2 | ½ | 110.60 (98–118) | 517.57 (409–457) | 106.70 (90–110) | 93.45 (70–90) | — |
| Human Thyrotropin Stimulating Hormone (micro international units/ml) | 5 | 1 | — | — | — | 59.36 (40–75) | 30.92 |

| | 37° Primary Assay Time Remote from Column, hr. | Room Temperature Incubation Time on Column, hr. | Control Sera | | |
|---|---|---|---|---|---|
| | | | Triiodo Thyronine Beckman Control Serum | Ortho I | Ortho II |
| Digoxin (ng/ml) | ½ | ½ | — | — | — |
| Thyroxine (μg/dl) | ½ | ½ | — | — | — |
| Triiodo thyronine (mg/dl) | 2 | ½ | 245.06 (165–225) | — | — |
| Human Thyrotropin Stimulating Hormone (micro international units/ml) | 5 | 1 | — | 7.95 (3.9–7.9) | 31.63 (23–39) |

*Values in ( ) are those obtained with the conventional double antibody method.

Table I compares the efficacy of employing the novel immunochemical composites within the scope of this invention in a solid phase column assay with the conventional prior art double antibody method in various immunoassay tests. As Table I indicates, the results obtained using the novel solid phase column method and immunochemical composites within the scope of this invention compare favorably with respect to the prior art method using said conventional double antibody method.

In addition to possessing all the advantages of solid phase immunoassay procedures, the novel solid phase column immunoassay procedure of this invention eliminates the need for centrifugation and also lends itself to automation.

Based on this disclosure, many other modifications and ramifications will naturally suggest themselves to those skilled in the art of immunoassay procedures. These are intended to be comprehended as within the scope of this invention.

The embodiments of the invention in which an exclusive property or privilege is claimed are defined as follows:

1. A method of separating free from bound fractions in a solid phase column immunoassay procedure of the type wherein a solution is contacted with a composite comprising an activated polysaccharide matrix covalently coupled to a primary antibody, wherein the improvement comprises contacting said solution with a composite comprising a derivatized, polysaccharide matrix covalently coupled to an antibody selected from a group consisting of primary and secondary antibodies via a bifunctional coupling agent having a formula

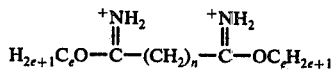

wherein $n$ is an integer from 1 to 6 and wherein $e$ is an integer from 1 to 2; and wherein said derivatized polysaccharide matrix comprises an activated, polysaccharide matrix coupled to an $\alpha,\omega$-diaminospacer via one of said $\alpha,\omega$-diaminospacer's amino groups.

2. The method of claim 1 wherein said immunochemical composite has a formula

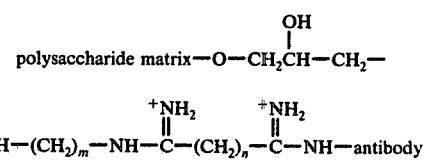

wherein $m$ is an integer from 1 to 12.

3. The method of claim 2 wherein said polysaccharide matrix is selected from a group consisting of cellulosic polymers, dextran polymers, agarose, and derivatives thereof, wherein $m$ is an integer from 4 to 6, and wherein $n$ is an integer from 4 to 6.

4. The method of claim 3 wherein said antibody is a secondary antibody.

5. The method of claim 4 wherein a primary immunoassay reaction is performed outside of said column and then an aliquot of said reaction mixture is incubated on said solid phase second antibody column.

6. The method of claim 5 wherein said immunoassay procedure is a radioimmunoassay procedure.

7. The method of claim 5 wherein an excess of said second antibody is present on said solid phase column.

8. The method of claim 7 wherein said immunoassay procedure is a radioimmunoassay procedure.

9. The method of claim 4 wherein said solid phase second antibody columns are loaded with primary antibody, labeled antigen, and sample, and wherein both said primary reaction and said incubation step with solid preparation of second antibody proceed simultaneously in the void volume of the column.

10. The method of claim 9 wherein said immunoassay procedure is a radioimmunoassay procedure.

11. The method of claim 4 wherein primary antibody is incubated on said solid phase second antibody column thereby producing a primary antibody column and wherein labeled antigen and sample are incubated on said primary antibody column.

12. The method of claim 11 wherein said immunoassay proceduere is a radioimmunoassay procedure.

13. The method of claim 1 wherein said immunoassay procedure is a radioimmunoassay procedure.

14. An immunochemical apparatus for separating free from bound fractions in a solid phase, immunoassay procedure of the type comprising a reaction vessel and a plurality of immunochemical composites, wherein each immunochemical composite comprises an activated polysaccharide matrix covalently coupled to a primary antibody, wherein the improvement comprises an immunochemical composite comprising a derivatized, polysaccharide matrix covalently coupled to an antibody selected from a group consisting of primary and secondary antibodies via a bifunctional coupling agent having a formula

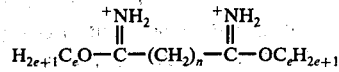

wherein $n$ is an integer from 1 to 6 and wherein $e$ is an integer from 1 to 2; and wherein said derivatized, polysaccharide matrix comprises an activated, polysaccharide matrix coupled to an $\alpha,\omega$-diaminospacer via one of said $\alpha,\omega$-diaminospacer's amino groups.

15. The immunochemical apparatus of claim 14 wherein said immunochemical composite has a formula

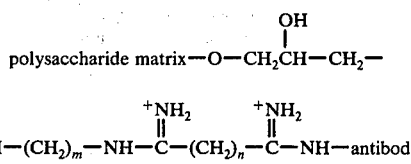

wherein $m$ is an integer from 1 to 12.

16. The immunochemical apparatus claim 15 wherein said polysaccharide matrix is selected from a group consisting of cellulosic polymers, dextran polymers, agarose, and derivatives thereof, wherein $m$ is an integer from 4 to 6 and wherein $n$ is an integer from 4 to 6.

17. The immunochemical apparatus of claim 16 wherein said antibody is a secondary antibody.

* * * * *